(12) United States Patent
Gaynor et al.

(10) Patent No.: US 8,540,736 B2
(45) Date of Patent: Sep. 24, 2013

(54) SPOOL CONFIGURED TO RETAIN SUTURE FOR A SUTURE SYSTEM

(75) Inventors: Allen Gaynor, Coon Rapids, MN (US); Thomas Kubalak, Wayzata, MN (US); Steven McClurg, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/491,609

(22) Filed: Jun. 8, 2012

(65) Prior Publication Data
US 2012/0316581 A1 Dec. 13, 2012

Related U.S. Application Data

(60) Provisional application No. 61/496,574, filed on Jun. 14, 2011.

(51) Int. Cl.
*A61B 17/04* (2006.01)

(52) U.S. Cl.
USPC .......................................... 606/146

(58) Field of Classification Search
USPC ........ 606/139, 144–150; 206/63.3; 242/172, 242/579, 580, 614, 118.4, 125–125.3
See application file for complete search history.

(56) References Cited

U.S. PATENT DOCUMENTS

| | | | |
|---|---|---|---|
| 2,457,379 A | 12/1948 | Kallenbach | |
| 2,824,709 A | 2/1958 | Macy | |
| 3,138,309 A | 6/1964 | Hulterstrum et al. | |
| 3,587,587 A | 6/1971 | Raskin | |
| 5,263,585 A | 11/1993 | Gardetto et al. | |
| 2003/0204195 A1 | 10/2003 | Keane | |
| 2011/0042245 A1* | 2/2011 | McClurg et al. | 206/63.3 |
| 2011/0046642 A1* | 2/2011 | McClurg et al. | 606/139 |
| 2011/0046645 A1* | 2/2011 | McClurg et al. | 606/145 |

FOREIGN PATENT DOCUMENTS

WO 2011020476 2/2011

OTHER PUBLICATIONS

ISR and Written Opinion from EPO dated Nov. 7, 2012 attached.

* cited by examiner

*Primary Examiner* — Darwin Erezo
*Assistant Examiner* — Shaun L David
(74) *Attorney, Agent, or Firm* — Coloplast Corp., Coloplast A/S; Nick Baumann

(57) ABSTRACT

A suture system spool is configured to retain suture having a suture diameter and tension the suture between a distal and proximal end portions of a suturing tool. The spool includes a monolithically formed disc defining a central opening that provides the disc with an inside diameter. The disc includes a base and a flap joined with the base at the inside diameter, and the flap extends from the inside diameter to an outer periphery of the disc to define a cavity between the flap and the base. The flap is spaced away from the base at a location between the inside diameter and the outer periphery of the disc by a factor of at least two times the suture diameter, and the flap is spaced away from the base at the outer periphery of the disc by a distance that is approximately equal to the suture diameter.

15 Claims, 9 Drawing Sheets

SPOOL CONFIGURED TO RETAIN SUTURE FOR A SUTURE SYSTEM

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon digitally palpates a desired location for placement of the suture and is unable to see the suture site.

Improved suturing instruments and improved methods of delivering sutures would be welcomed by the surgical staff.

SUMMARY

One aspect provides a suture system spool configured to retain suture having a suture diameter and tension the suture between a distal end portion and a proximal end portion of a suturing tool. The spool includes a monolithically formed disc defining a central opening that provides the disc with an inside diameter. The disc includes a base and a flap joined with the base at the inside diameter, and the flap extends from the inside diameter of the disc to an outer periphery of the disc to define a cavity between the flap and the base. The flap is spaced away from the base at a location between the inside diameter and the outer periphery of the disc by a factor of at least two times the suture diameter, and the flap is spaced away from the base at the outer periphery of the disc by a distance that is approximately equal to the suture diameter.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

Embodiments provide a suturing tool having a needle housed in a proximal end portion of a head of the tool, where the needle is adapted to be deployed longitudinally out of the proximal end portion of the head through a mass of tissue to subsequently grasp a suture assembly. The needle retracts after engaging the suture assembly and pulls the suture assembly back along the needle path or channel formed in the tissue. In this manner, the needle moves through the tissue, grasps the suture assembly, and retracts the suture assembly through the tissue to complete a "stitch" in the tissue.

Embodiments provide a flexible and compressible spool that is configured to retain a length of suture for use by a suturing tool. The spool is configured to prevent the free spooling of the suture out of the spool by, for example, providing a flap or a lip that impinges against the suture. The flap provides a frictional force that allows only a single strand of the suture to be unwound from the spool at any one time. The spool thus provides means for stripping the suture a single winding at a time out of the cavity.

Figure 1:
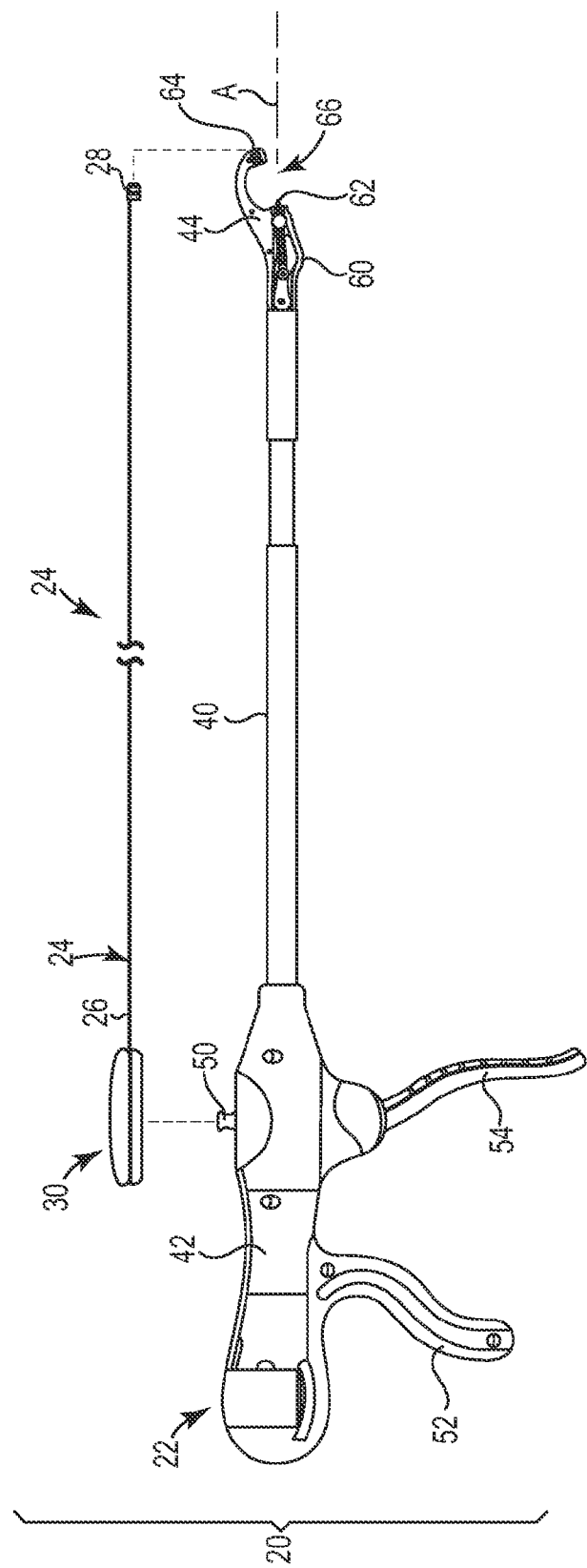
FIG. 1 is a side view of one embodiment of a suture system including a tool and a spool retaining suture.

FIG. 1 is a side view of one embodiment of a suture system 20. The suture system 20 includes a tool 22, a suture assembly 24 including a length of suture 26 attached to a suture clip 28, and a spool 30 that retains multiple windings of the suture 26. The spool 30 is attachable to a proximal portion (post 50) of the tool 22 and the suture clip 28 is attachable to a distal portion 64 of the tool 22 in a manner that maintains the suture 26 between the proximal 50 and distal portions 64 of the tool 22.

The tool 22 includes a shaft 40 attached between a handle 42 and a head 44. The shaft 40 generally provides a major longitudinal axis of the tool 22 and is oriented along a longitudinal axis A. In one embodiment, the shaft 40 is a rigid shaft that is not bendable. In one embodiment, shaft 40 is a flexible shaft that is configured to be bent laterally left and right and vertically up and down and through all points in-between.

The handle 42 includes a post 50 that is sized and configured to frictionally engage with the spool 30, a rigid thumb brace 52, and a movable actuator 54 located proximal the thumb brace 52. The handle 42 is configured to be grasped by a hand of a surgeon with the thumb wrapped around the thumb brace 52 and the actuator 54 operated by one or more fingers. Movement of the actuator 54 moves a rod or other mechanism located within the shaft 40 to cause movement of the needle 62 back and forth across throat 66.

The head 44 of the tool 22 includes a proximal portion 60 housing a needle 62 and a distal end 64 spaced apart from the proximal portion 60 by the throat 66. The actuator 54 communicates with the needle 62 by a rod 72 (FIG. 2) located inside the shaft 40 that moves the needle 62 between the proximal portion 60 and the distal end 64 of the head 44. In one embodiment, the needle 62 moves along the longitudinal axis A. In one embodiment, the distal end 64 is located off axis relative to the longitudinal axis A and the needle 60 moves in a direction that is not parallel with the longitudinal axis A such that the needle moves off axis (i.e., "shunts") relative to the longitudinal axis A.

Figure 2:
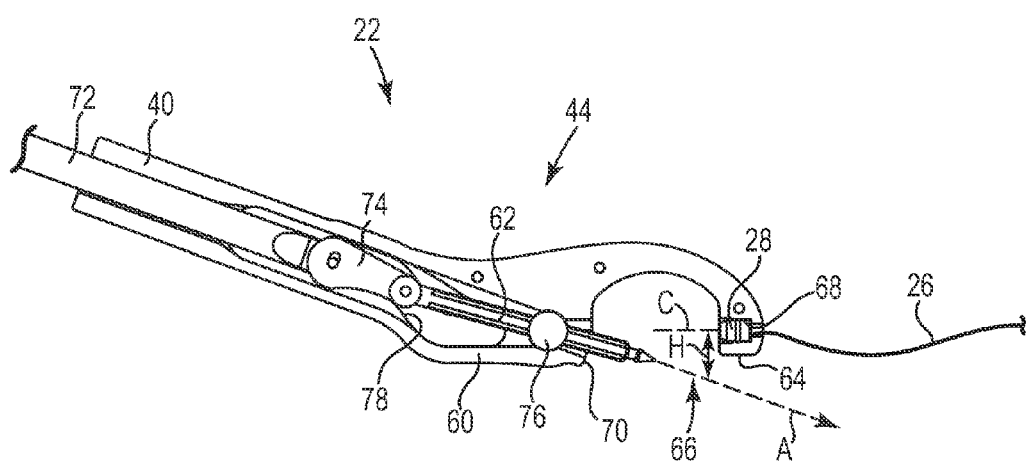
FIG. 2 is a side sectioned view of a head of the tool illustrated in FIG. 1.

FIG. 2 is a side sectional view of the head 44 of the tool 22 showing the needle 62 partially extending from a needle exit port 70 in response to the activation of actuator 54 (FIG. 1). The distal end 64 of the head 44 provides a cavity 68 that is sized to receive the suture clip 28. The tool 22 operates to move the needle 62 through tissue to form a channel in the tissue, engage the needle 62 with the suture clip 28, and withdraw the suture clip 28 from the cavity 68 and back through the tissue channel. The tool 22 operates to pull the suture clip 28 and the suture 26 across the throat 66 to place the suture 26 into the tissue.

The needle 62 moves in response to movement of the actuator 54 (FIG. 1) via a rod 72 that is located axially within the shaft 40 that communicates between the actuator 54 and the needle 62. In particular, the rod 72 is attached to a link 74 that is attached to the needle 62, and the needle 62 is engaged with a guide pin 76. The guide pin 76 is configured to rotate to allow the link 74 to move within a trace 78. For example, in one embodiment the distal end 64 is radially spaced apart from the longitudinal axis A by a distance H and the guide pin 76 rotates to allow the link 74 to move within the trace 78. The movement of the link 74 shunts the leading end of needle 62 away from the longitudinal axis A to a second direction aligned with an axis C that extends through cavity 68. This offset configuration of the distal end 64 of the head 44 provides the tool 22 with an improved mechanical advantage over linear tools, which allows the tool 22 to secure suture into tough tissue, such as ligaments.

Figure 3:
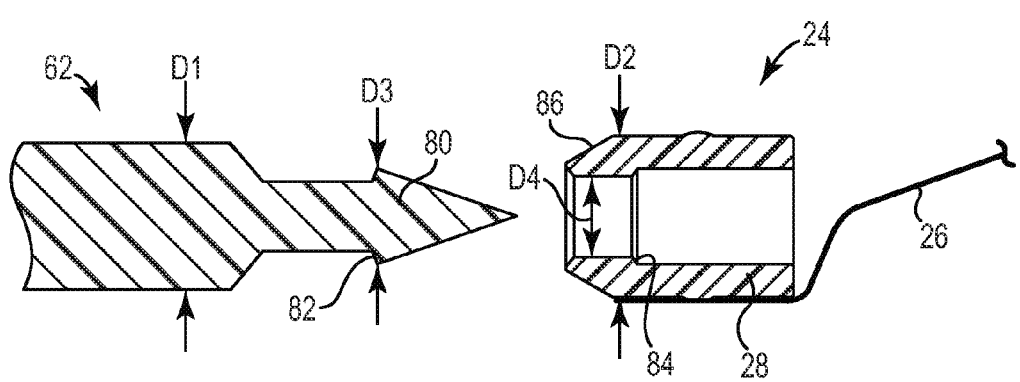
FIG. 3 is a cross-sectional view of a needle of the tool positioned for engagement with a suture clip of the suture assembly.

FIG. 3 is a side view of the needle 62 aligned for engagement with the suture clip 28 of the suture assembly 24. The suture clip 28 is attached to the suture 26. In one embodiment, the suture clip 28 is molded from plastic to integrally capture the suture 26. Suitable plastic materials for fabricating the suture clip 28 include polypropylene, polysulfone, urethane, or polyetherimide as examples and the suture 26 is selected to be compatible with these materials.

In one embodiment, the suture clip 28 is fabricated from metal and attached to one of a variety of sutures, for example a thermoplastic suture, a resorbable suture, body-absorbable suture, a multi-filament suture, a mono-filament suture, or a bioabsorbable suture. Bioabsorbable sutures are generally fabricated from a material having a melting point that is incompatible with overmolding or welding to a polypropylene suture clip 28. A metal suture clip 28 is compatible with attachment to all forms of suture material, including bioabsorbable suture. To this end, a metal suture clip 28 is suited for attachment to fine diameter suture having a suture size of 0 or larger diameter suture having a suture size of 0 or larger.

Suitable suture is available from Teleflex, Limerick, Pa. or CP Medical, Portland, Oreg. Other suitable suture is available from Ethicon™, a J & J Company located in Somerville, N.J., and include resorbable and other sutures such as Monocryl™ (polyglycaprone 25) sutures, coated Vicryl™ (polyglactin 910) sutures, Ethicon Plus™ Sutures, or polydioxanone sutures as examples. Examples of suitable body-absorbable sutures are the Caprosyn™ Polysorb™, and Biosyn™ absorbable sutures available from Covidien, Mansfield, Mass.

The needle 62 is formed from metal such as stainless steel or a shape memory alloy such as NITINOL (Nickel Titanium Naval Ordinance Laboratory), or titanium as examples. In one embodiment, the needle 62 is shaped to promote secure engagement with the suture clip 28 and a leading end 80 is formed to have a conical point with a shoulder 82 that is sized to be pressed into engagement with a flange 84 formed inside the suture clip 28. The guide pin 76 (FIG. 2) is provided to disengage the suture clip 28 from the needle 62 as the needle 62 moves rearward through the guide pin 76.

The conical point of the needle 62 is configured to form a channel when advanced through tissue, and the suture clip 28 is sized to be pulled through the channel in the tissue made by the needle 62. In one embodiment, the leading end portion 86 of the suture clip 28 is chamfered and the needle 62 is configured to draw the chamfered (or truncated) leading end portion 86 through the tissue channel.

In one exemplary embodiment, the needle 62 has a first diameter D1 and the suture clip 28 has a diameter D2, were diameter D1 is equal to or greater than diameter D2. In this manner, the suture clip 28 is sized to follow needle 62 and be retracted through the channel formed in the tissue by needle 62.

The needle 62 is sized to frictionally engage with the recess formed in the suture clip 28. For example, in one embodiment the leading end 80 of the needle 62 has a diameter D3 that is slightly greater than a diameter D4 formed in the channel of the suture clip 28. In this manner, when the leading end 80 of the needle 62 is inserted into recess, the shoulder 82 of the needle 62 seats with the shoulder 82 to allow the needle 62 to engage with the suture clip 28.

Figure 4:
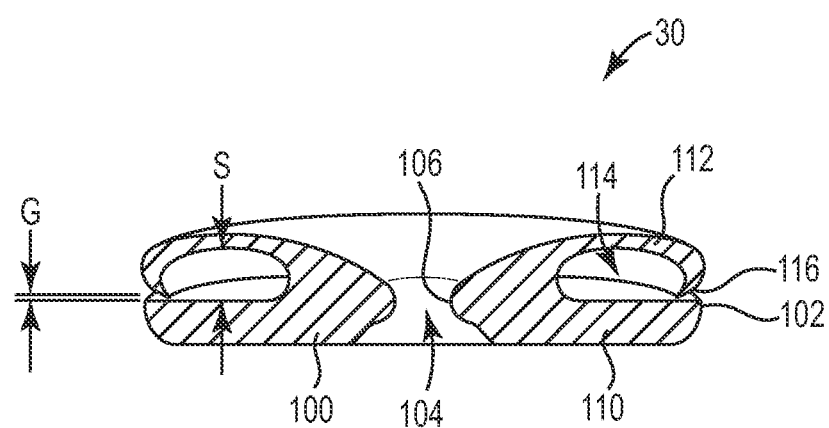
FIG. 4 is a cross-sectional view of one embodiment of the spool illustrated in FIG. 1.

FIG. 4 is a cross-sectional view of the spool 30. In one embodiment, the spool 30 is a monolithically formed disc 100 having an outer periphery 102 and a central opening 104 that provides the disc 100 with an inside diameter 106. The spool 30 includes a base 110 and a flap 112 joined to the base 110 at the inside diameter 106. The flap 112 extends from the inside diameter 106 to the outer periphery 102 to define a cavity 114 between the flap 112 and the base 110. The cavity 114 provides a cavity height S that is sized to retain multiple windings of the suture 26 (See FIG. 5A).

The flap 112 is configured to prevent more than one strand of the suture 26 from unspooling from the cavity 114 as the suture 26 is unwound from the spool 30. For example, in one embodiment the flap 112 defines an arc that locates an outer radial end 116 of the flap 112 within a gap distance G of the base 110. The outer radial end 116 of the flap 112 is configured to impinge or pinch against the suture 26 to provide a frictional resistance force that prevents more than one strand of the suture 26 from exiting the cavity 114 during suture unwinding. Unspooling of the suture 26 is undesirable.

Unspooling means that multiple strands of the suture 26 exit the cavity together as the suture 26 is unwound from the spool 30.

Embodiments of the spool 30 reduce or eliminate the undesirable unspooling of the suture 26 from out of the cavity 114 of the spool 30. In this manner, the base 110 and the flap 112 combine to provide the spool with means for stripping the suture 26 a single winding at a time from the cavity 114.

In one embodiment, the flap 112 is cantilevered from the inside diameter 106 of the disc 100. The flap 112 is configured to be flexible and so provided to flex away from the base 100 to allow the suture 26 to deflect the flap 112 upward as the suture 26 is removed from the cavity 114. In addition, the flap 112 provides a friction force against the suture 26 that reduces or eliminates the undesirable unspooling of suture 26 out of the cavity 114.

In one embodiment, an exterior surface of the flap 112 is curved and an exterior surface of the base 110 is substantially planar.

The base 110 and a flap 112 are formed as a single integral unit such that the disc 100 is a monolith formed from a flexible material. Suitable materials for fabricating the disc 100 include thermoplastic elastomers (TPE) such as the TPE available from ExxonMobil, Houston, Tex. as Sanoprene™ elastomer or a butadiene-based butyl rubber (BUNA).

Figure 5A:
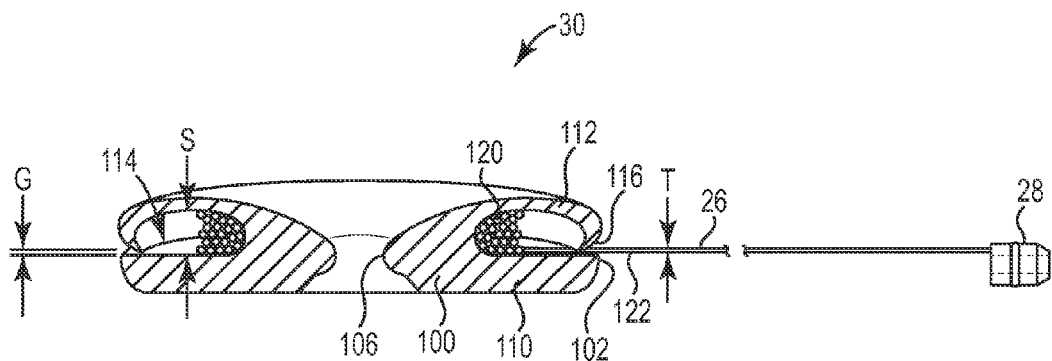
FIG. 5A is a cross-sectional view of one embodiment of the spool illustrated in FIG. 4 with a portion of suture of the suture loaded into a cavity of the spool.

FIG. 5A is a cross-sectional view of the spool 30 loaded with multiple windings 120 of the suture 26, where the suture 26 has a suture thickness or suture diameter of T.

In one embodiment, a tail end portion 122 of the multiple windings 120 of the suture 26 projects out of the cavity 114 and is pinched between the flap 112 and the base 110 at the outer periphery 102 of the disc 100. In this manner, the outer radial end 116 of the flap 112 is positioned to pinch against the tail end portion 122 of the suture 26 to frictionally resist unwinding of more than one strand of the suture 26 at a time from the cavity 114.

In one embodiment, the flap 112 is spaced away from the base 110 at a location between the inside diameter 106 and the outer periphery 102 to provide the cavity height S with a dimension that is a factor of at least 2 times the suture diameter T, and the end 116 of the flap 112 is spaced away from the base 110 by a gap distance G that is selected to be substantially equal to the suture diameter. In other words, $S>2T$ and $G \sim T$.

Figure 5B:
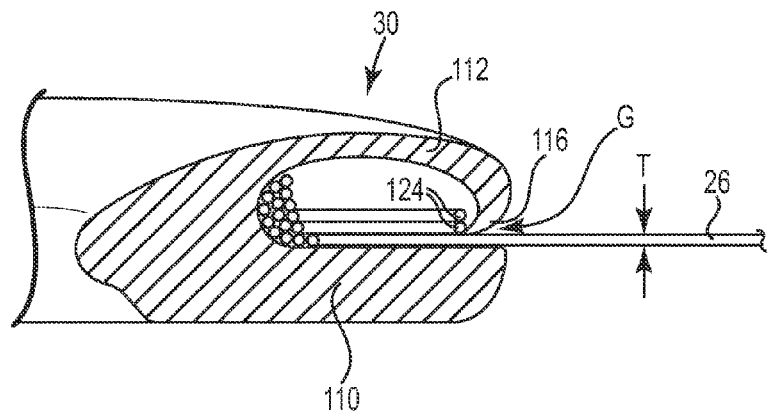
FIG. 5B is a cross-sectional view of a gap formed in the spool that meters the suture as it exits the spool to allow only a single strand of the suture to be unwound off of the spool.

FIG. 5B is a cross-sectional view of the outer radial end 116 of the flap 112 cooperating with the base 110 to reduce or eliminate undesirable unspooling of suture 26 off of the spool 30. The gap distance G is selected to be smaller than the suture diameter of T such that the outer radial end 116 of the flap 112 allows only a single strand of the suture 26 to be unwound off of the spool 30. In this manner, the end 116 of the flap 112 is a limiter that prevents the wound strands 124 from exiting the spool 30 until after the strand of suture 26 moves through the gap G.

In one embodiment, the gap G to selectively sized to be less than the suture diameter (e.g., $G<T$) and the flap 112 is flexible to allow only a single strand of the suture to be metered past the end 116 of the flap 112 to be unwound from the cavity 114.

Figure 5C:
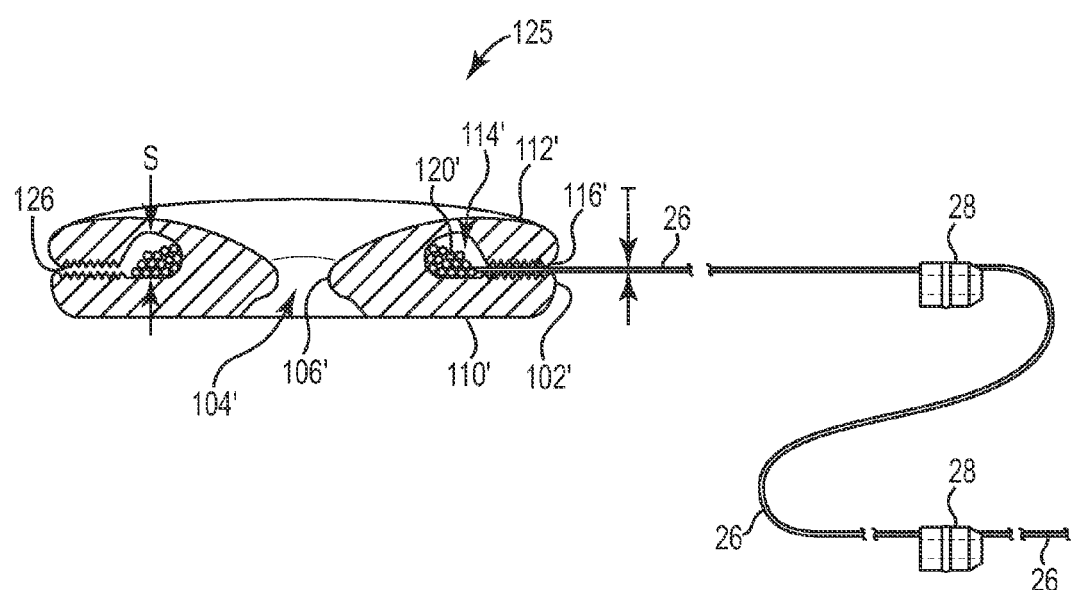
FIG. 5C is a cross-sectional view of one embodiment of a spool including serrated teeth, with the spool retaining suture attached to multiple suture clips.

FIG. 5C is a cross-sectional view of one embodiment of a spool 125 including serrated teeth 126, with the spool 125 retaining a suture 26 attached to multiple suture clips 28. The spool 125 has an outer periphery 102' with a central opening 104' that provides the disc with an inside diameter 106'. The spool 125 includes a base 110' and a flap 112' joined to the base 110' at the inside diameter 106'. The flap 112' extends from the inside diameter 106' to the outer periphery 102' to define a cavity 114' between the flap 112' and the base 110'. The cavity 114' provides a cavity height S that is sized to retain multiple windings 120' of the suture 26. In one embodiment, inside surfaces of the flap 112' and the base 110' form serrated teeth 126 that are configured to grasp the suture 26 after the needle 62 engages with one of the multiplicity of suture clips 28 attached to the suture 26. In one embodiment, the spool 125 is monolithically formed as a single integral unit.

Figure 6:
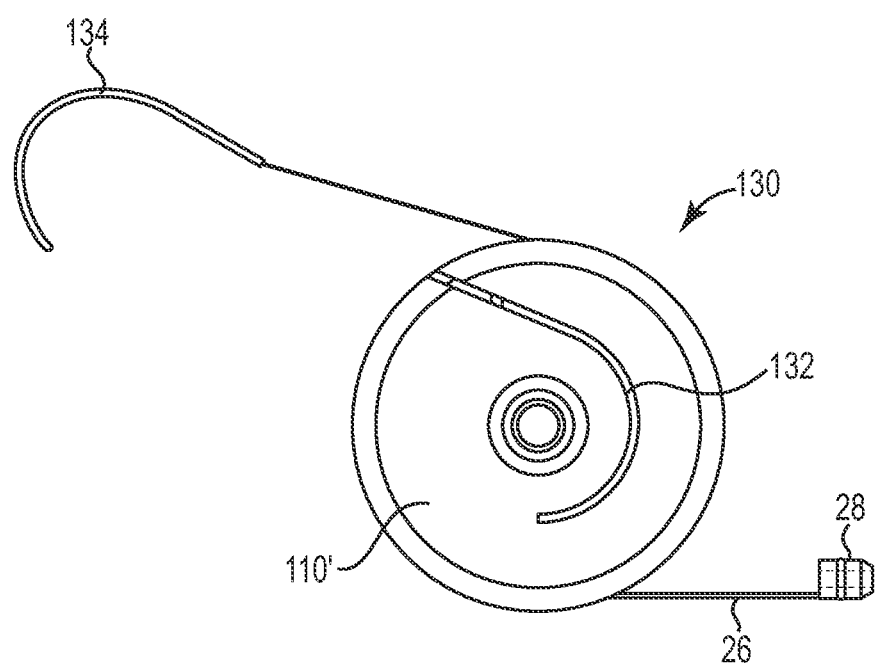
FIG. 6 is a bottom view of one embodiment of a spool configured to retain suture.

FIG. 6 is a bottom view of one embodiment of a spool 130. The spool 130 includes a recess 132 formed in an exterior surface of a base 110'. In one embodiment, the suture clip 28 is attached to one end of the suture 26 and a suturing hook 134 is attached to an opposite end of the suture 26. The recess 132 provides a convenient and safe storage place for the crescent needle 134.

Figure 7:
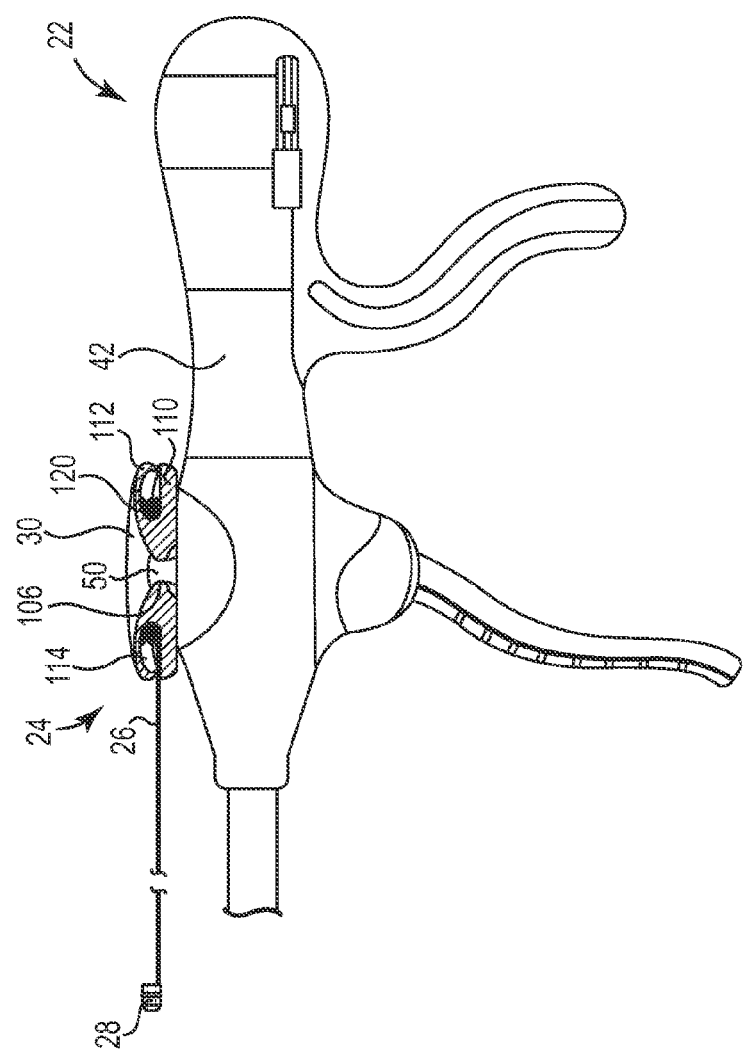
FIG. 7 is a cross-sectional view of one embodiment of the spool illustrated in FIG. 5A coupled with a handle of the tool illustrated in FIG. 1.

FIG. 7 is a partial cross-sectional view of spool 30 loaded with the suture assembly 24 and attached to the post 50 of the tool 22. In one embodiment, the inside diameter 106 of the spool provides a compressible surface that flexes for frictional engagement of the spool 30 to the post 50. The cavity 114 retains multiple windings 120 of the suture 26. The flap 112 and the base 110 combine to provide a meter or a limiting device that prevents the suture 26 from unspooling from the cavity 114.

A portion of the suture 26 extends from the cavity 114 to allow the suture clip 28 to be engaged in the cavity 68 formed in the head 44 of the tool 22 (FIG. 2). The spool 30 is attached to the post 50 of the handle 42. In this manner, the spool 30 retains multiple windings 120 of the suture 26 and also maintains a suture 26 in tension between the head 44 and a handle 42 of the tool 22.

Figure 8:
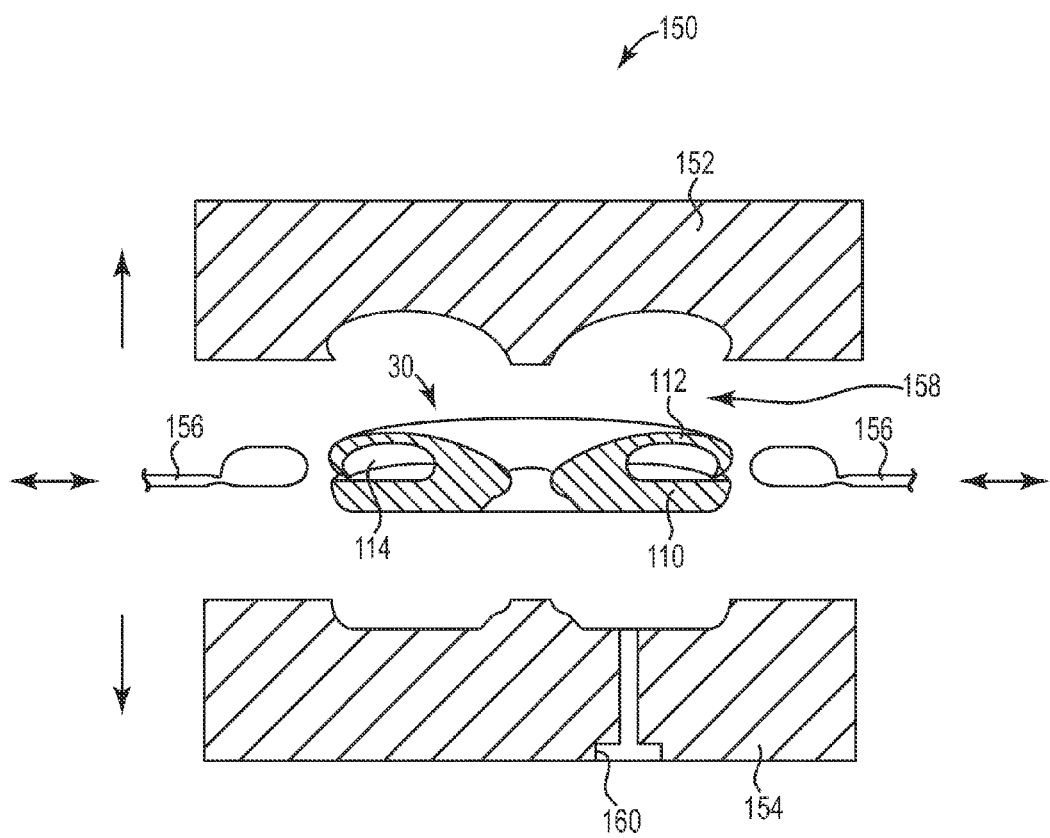
FIG. 8 is a cross-sectional view of one embodiment of a mold provided for fabricating the spool illustrated in FIG. 4.

FIG. 8 is a cross-sectional view of one embodiment of a mold 150 provided for fabricating the spool 30 illustrated in FIG. 4. The mold 150 includes a top section 152 that mates with a bottom section 154 and a central section 156 that moves radially inward/outward relative to the section 152, 154. The top section 152 is configured to fabricate an image of the upper surface (or flap 112) of the mold 30 and the bottom section 154 is configured to fabricate an image of the lower surface (or base 110) of the mold 30. The central section 156 is shaped to replicate the cavity 114.

In one acceptable molding process, the top section 152 is lowered and the bottom section 154 is raised to seal against the central section 156 that is inserted centrally within the mold 150. Mold material is injected into the cavity 158 of the mold 150 through a port 160 to provide a replication of the spool 30. The port 160 is formed in the bottom section 154, although other locations for port 160 are also acceptable. After injection of the mold material, the top section 152 is raised and the bottom section 154 is lowered relative to the central section 156 to separate the mold 150, and the central section 156 is moved radially outward to form the cavity 114 inside the spool 30. In one embodiment, the mold material is a flexible material, such as one of the elastomers described above, which allows the central section 156 that is larger than the gap distance G (FIG. 4) to be withdrawn out of the narrower gap distance G. In particular, the flexible material of the flap 112 and the base 110 allows these components to be displaced as the central section 156 is withdrawn, which allows the relatively tall cavity 114 to be formed between the flap 112 and the base 110. In addition, the flexible material allows the flap 112 to recover or spring back after the central section 156 is withdrawn, which locates the flap 112 at the gap distance G away from the base.

Embodiments provide a spool that is configured to retain a length of suture for use by a suturing tool, where the spool is configured to prevent the free spooling of the suture out of the spool by. Embodiments include a flap that flexes to pinch against the suture. The flap thus provides a frictional force that allows only a single strand of the suture to be unwound from the spool at any one time.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A suture system spool configured to retain suture having a suture diameter and tension the suture between a distal end portion and a proximal end portion of a suturing tool, the spool comprising:
   a monolithically formed disc defining a central opening that provides the disc with an inside diameter, the disc including a base and a flap joined with the base at the inside diameter, the flap extending from the inside diameter of the disc to an outer periphery of the disc to define a cavity between the flap and the base;
   wherein the flap is spaced away from the base at a location between the inside diameter and the outer periphery of the disc by a factor of at least two times the suture diameter, and the flap is spaced away from the base at the outer periphery of the disc by a distance that is approximately equal to the suture diameter and
   wherein the flap is cantilevered from the inside diameter of the disc, the flap configured to flex away from the base to allow the suture to be removed from the cavity.

2. The suture system spool of claim 1, wherein a gap is formed between the flap and the base at the outer periphery of the disc, and the gap is less than the suture diameter.

3. The suture system spool of claim 1, wherein an outer peripheral end portion of the flap is configured to flex away from the base at the outer periphery of the disc to allow only a single strand of the suture to be unwound from the cavity.

4. The suture system spool of claim 1, wherein a tail end portion of the multiple windings of the suture projects out of the cavity and is pinched between the flap and the base at the outer periphery of the disc.

5. The suture system spool of claim 1, wherein the suture includes a suturing hook connected to an end of the suture and an exterior surface of the base defines a recess that is sized to receive the suturing hook.

6. The suture system spool of claim 1, wherein an exterior surface of the flap is curved and an exterior surface of the base is substantially planar.

7. The suture system spool of claim 1, wherein the inside diameter formed by the central opening in the disc provides a compressible surface that is attachable to a post at the proximal end portion of the suturing tool.

8. A suture system configured to place suture in tissue, the suture system comprising:
   a tool comprising a handle and a head located distal the handle, the head having a proximal portion housing a needle and a distal end spaced apart from the proximal portion by a throat, the needle is movable through a needle exit port formed in the proximal portion of the head to a cavity formed in the distal end of the head;
   a suture assembly comprising a suture connected to a suture clip, the suture having a suture diameter and the suture clip insertable into the cavity formed in the distal end of the head; and
   a suture spool according to any one of claims 1-7.

9. The suture system of claim 8, wherein the flap is spaced away from the base at the outer periphery of the spool by a distance that is less than the suture diameter.

10. The suture system of claim 8, wherein the cavity has a height extending between the flap and the base that is at least two times the suture diameter.

11. The suture system of claim 8, wherein an end of the flap flexes to provide a limiter that frictionally contacts the suture.

12. The suture system of claim 11, wherein the limiter prevents unspooling of the suture from out of the cavity.

13. The suture system of claim 8, wherein an inside surface of the flap comprises serrated teeth.

14. The suture system of claim 13, wherein an inside surface of the base comprises serrated teeth.

15. The suture system of claim 8, wherein the suture is connected to a plurality of suture clips.

* * * * *